United States Patent [19]

Mayer et al.

[11] Patent Number: 4,852,389
[45] Date of Patent: Aug. 1, 1989

[54] SYSTEM FOR CONTROLLED HUMIDITY TESTS

[75] Inventors: Daniel W. Mayer, Arden Hills; Craig K. Loebig, Elk River; Wayne K. Savick, Eden Prairie, all of Minn.

[73] Assignee: Modern Controls, Inc., Minneapolis, Minn.

[21] Appl. No.: 174,195

[22] Filed: Mar. 28, 1988

[51] Int. Cl.⁴ .................. G01N 15/08; G01M 3/00
[52] U.S. Cl. .................................................... 73/38
[58] Field of Search ............... 73/38, 64.3, 19, 23, 73/73, 23

[56] References Cited

U.S. PATENT DOCUMENTS

| | | | |
|---|---|---|---|
| 3,286,509 | 11/1966 | Gluckman et al. | 73/38 |
| 3,498,110 | 3/1970 | Brun | 73/38 |
| 3,590,634 | 7/1971 | Pasternak | 73/38 |
| 3,604,246 | 9/1971 | Toren | 73/38 |
| 3,760,773 | 9/1973 | Christensen | 73/38 |
| 3,926,561 | 12/1975 | Lucero | 73/38 |
| 4,464,927 | 8/1984 | Reid | 73/38 |
| 4,557,138 | 10/1985 | Dumitriu-Valcea et al. | 73/38 |
| 4,656,865 | 4/1987 | Callan | 73/38 |
| 4,660,411 | 4/1987 | Reid | 73/38 |
| 4,759,882 | 7/1988 | Reid | 261/16 |

*Primary Examiner*—Hezron E. Williams
*Attorney, Agent, or Firm*—Paul L. Sjoquist

[57] ABSTRACT

A system for controlled humidity tests wherein gas transmission through a barrier may be measured, including apparatus for controllably mixing a dry gas and wet gas, for conveying the mixed gas to a test chamber or chambers for measurement of relative humidity and gas transition through a barrier, including gas transmission conduits having a pressure drop of less than 1 percent of ambient pressure, and including conduit temperature controls to maintain a controlled first temperature in the test chamber or chambers, and controlled higher temperatures in all other gas conduits.

13 Claims, 7 Drawing Sheets

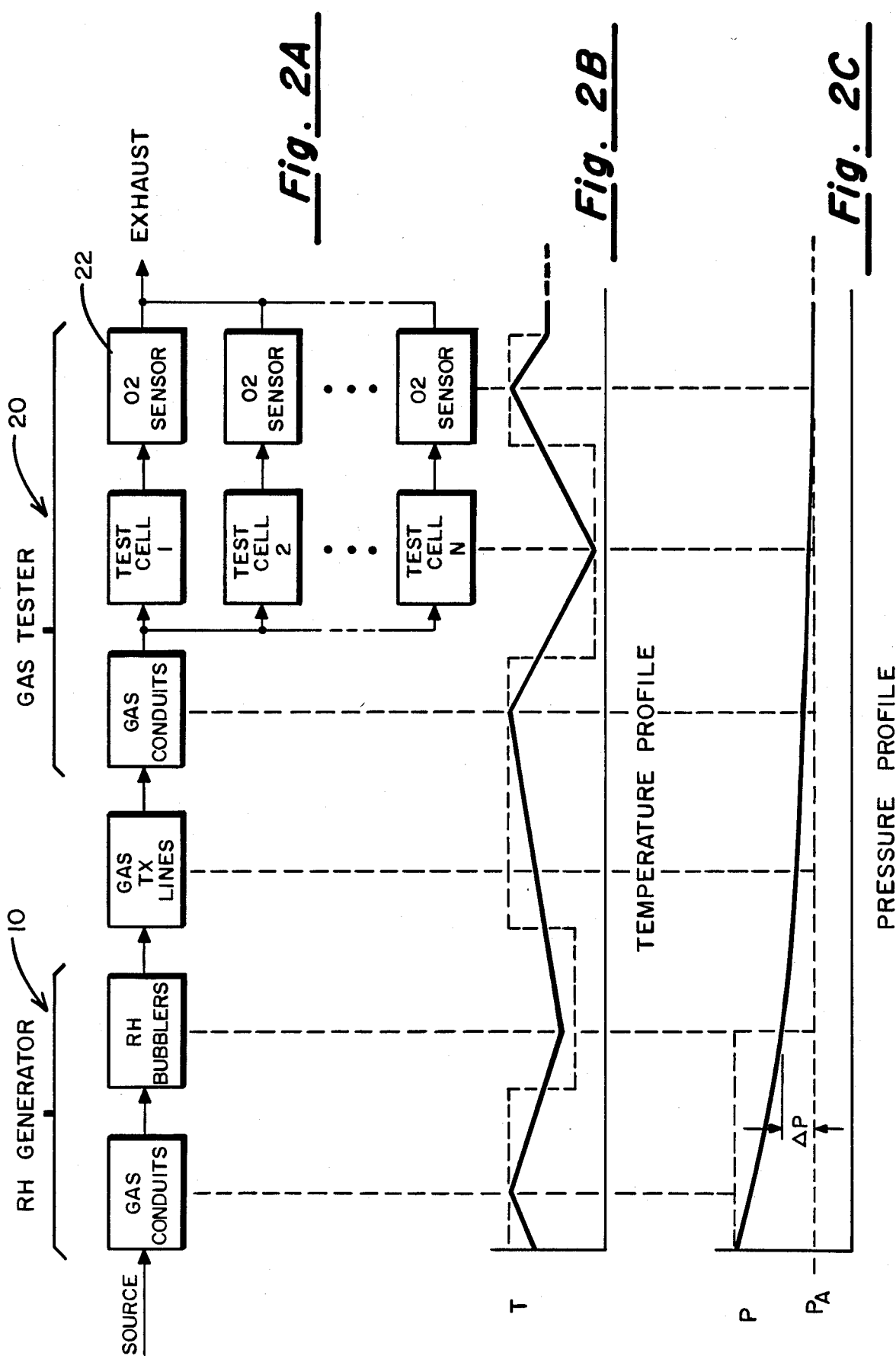

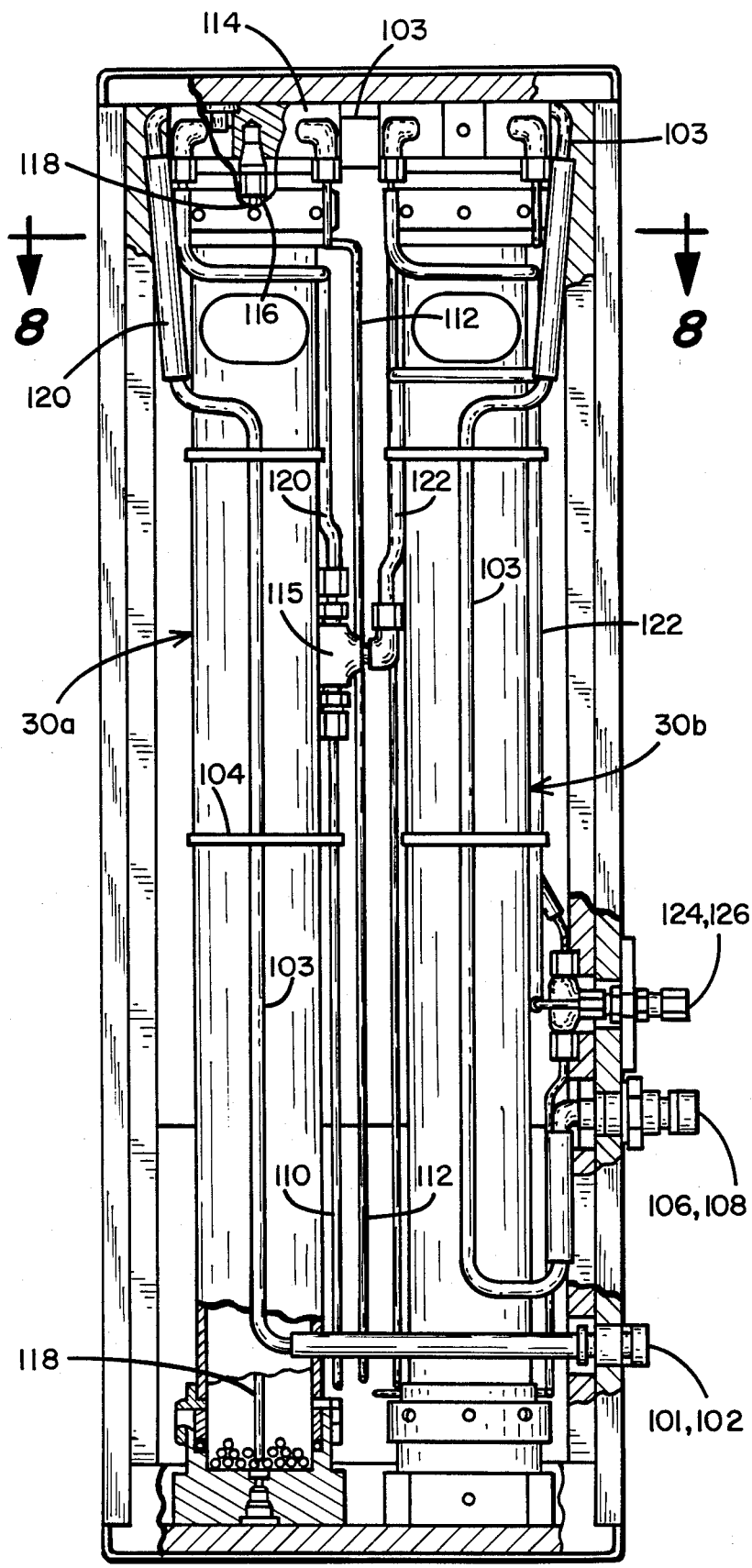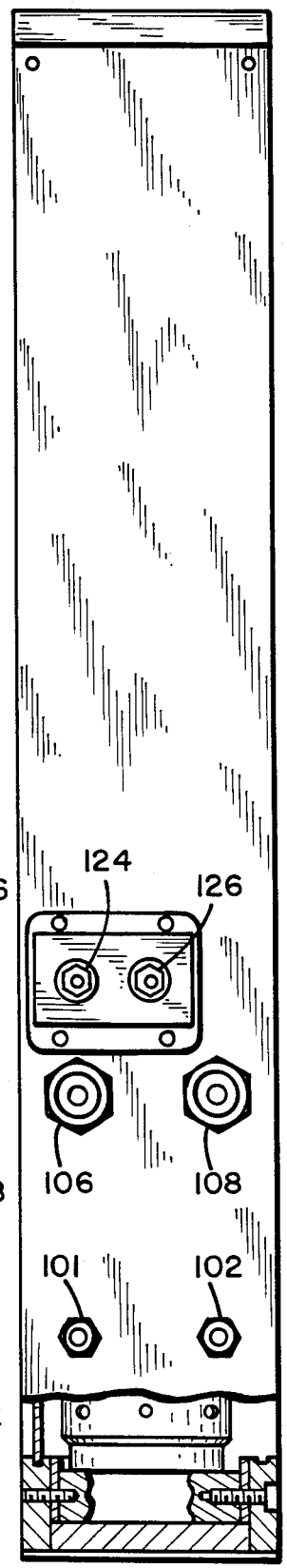
*Fig. 7A*  *Fig. 7B*

SYSTEM FOR CONTROLLED HUMIDITY TESTS

BRIEF DESCRIPTION OF THE INVENTION

The present invention relates generally to a system for enabling controlled vapor pressure tests with respect to gas analysis; more particularly, the invention relates to a system for measuring gas transmission rates through barriers under conditions of controlled and precisely known relative humidities. The system is particularly adaptable for measuring oxygen transmission rates through permeable barriers under controlled water vapor humidity conditions, although the principles of the system may equally be applied to vapor pressures produced by other liquids.

BACKGROUND OF THE INVENTION

The packaging industry has an interest in producing packaging materials, in particular plastic packaging materials, which may be substituted for older and more conventional materials such as metal or glass. Packaging made from metal or glass materials are virtually impermeable to moisture and humidity; packaging materials made from plastic materials are virtually always susceptible to gas and vapor permeability problems. Plastic packaging materials are oxygen permeable, and if the product carried by the packaging is oxygen sensitive, changes in taste, odor, color, texture and potency may occur within the package to degrade the quality of the product. These effects create a substantially reduced shelf life for packaged materials, in particular packaged food products, and there is therefore a need to properly evaluate such packaging materials to determine the permeability characteristics of the materials, so that the reasonable shelf life of the packaging may be predicted. Stated another way, accurately calibrated permeability tests enable the dvelopment and evaluation of various packaging materials, in order that materials displaying the best shelf life characteristics may be chosen for packaging.

It is known that the oxygen permeability characteristics of certain plastic materials is greatly affected by relative humidity conditions. It is also known that relative humidity is greatly affected by temperature and pressure variations in the environment. For example, a 1° C. change in room temperature can result in a 5 percent change in relative humidity. Certain materials, such as glassine, cellophane, ethylene vinyl alcohol (EVOH), and certain forms of nylon exhibit oxygen permeability characteristics which are strongly affected by the presence of water. EVOH, in particular, is an excellent oxygen barrier under "dry" conditions, but becomes a relatively poor oxygen barrier under "wet" conditions; furthermore, the oxygen transmission rate of this material is not linear over a range of relative humidity. For example, the oxygen transmission rate through 0.6 mil. EVOH is practically zero at a 50 percent relative humidity or below, is about 20 cubic centimeters per square meter per day ($cc/m^2/d$) at 90 percent relative humidity, and is in excess of 125 $cc/m^2/d$ at about 98 percent relative humidity. Therefore, in order to properly evaluate the oxygen transmission rate through materials such as EVOH, it becomes important to be able to quantify relative humidity in terms more definitive than "dry" or "wet". In particular, it is necessary to effectively measure oxygen permeability of barrier materials under very high, precisely defined relative humidity conditions, preferably in the range of 70-95 percent relative humidity (RH).

One method which has been proposed as an approach for measuring oxygen transmission rate through moisture sensitive barrier films is described as the "sandwich method." This method is described by R. C. Wood, in the *Journal of Testing and Evaluation*, JTEVA, Volume 12, No. 3, May 1984 (pages 149-151). The method requires the assembly of a thin, multi-layer structure in which the test specimen is enclosed between moist absorbent tissues and cover sheets of an oxygen-transparent plastic material. This "sandwich" is clamped between the two halves of a gas transmission cell which measures oxygen permeability through the test specimen. The absorbent tissues are saturated with various solutions, and an assumption is made concerning the relative humidity environment which this arrangement provides. The test gases used in conjunction with the method are dry, and the method has been used with some limited success with certain types of test specimens.

For any system to have practical utility in the field of measuring gas transmission rates through barriers under variable temperature and humidity conditions, there are a number of stringent and competing objectives to be met. First, the system must be capable of operating under a wide range of test condition temperatures; second, the system must be capable of operating under a wide range of vapor pressure test conditions; third, the system must be capable of conducting tests under any combinations of temperature and vapor pressure within the test ranges set forth. In addition, the system must be operable under normal laboratory temperature and relative humidity conditions, and it must be producible at a cost which can be justified by the test results sought. Under all of the foregoing parameters, the system must accurately measure the permeability of a test gas through a test membrane, and prior art systems have been unable to accomplish this without sacrificing one or more of these parameters.

Underlying all of the requirements for the design of such a system is the base requirement that the lowest temperature in the system must be greater than the saturated vapor pressure temperature of the vapor being generated by the system. This parameter must be complied with to assure that there will be no condensation in the system, for condensation anywhere within the system will render the system useless. The ability to satisfy this parameter, as well as the other requirements for the system, is dictated by how the temperature is controlled in the system; in particular, by controlling how and where the lowest temperature occurs in the system. In principle it is desirable to have all parts of the system at a single temperature, wherein the entire system temperature may be set to, the desired test temperature for purposes of conducting the necessary tests. The remaining test conditions could then be satisfied by merely mixing the saturated vapor with the carrier gas to the desired level, usually measured in parts per million, and delivering this mixture to the test cell for permeability measurements. Unfortunately, the system having this characteristic would undoubtably violate the cost parameter restriction, because the state of the art in instrument design prohibits the temperature control of all critical parts of the system under reasonable cost constraints.

All known prior art systems have been forced to sacrifice one or more of the optimum design objectives in order to produce a system which has at least some utility in this field. For example, a Japanese company, Hisco, has developed a system for testing oxygen permeability, designated Model RH-1, and a system for testing carbon dioxide permeability, designated RH-2, by developing a bubbler device which is temperature controlled by a water bath. The output of this bubbler device is connected to a gas testing apparatus manufactured by the assignee of the present invention, under the trade designation OX-TRAN, and a humidity sensor is connected to the output of the gas test cell in the OX-TRAN device. The system operates under the assumption that the humidity measured at the output of the test cell is equal to the humidity within the test cell, although no control is maintained over temperature.

Another system has been developed by a U.S. company, 'Atory, Inc., under the model designation A3 GHU, which utilizes a "two flow method." This system requires the mixing of a gas with no vapor content with a gas that is saturated by vapor to a desired mixing ratio. This mixed gas is delivered to a test cell for measuring permeability through a membrane. Unfortunately, there is no control of temperature in the system, and the system is therefore susceptible to condensation, although a relative humidity sensor is placed at the output of the humidity generating portion of the system, and another relative humidity sensor is placed in a return line to the humidity portion of the system. The operating theory is apparently that if the two sensors measure the same relative humidity, it can be presumed that the relative humidity in the test cell is known. However, without control over temperature this assumption is invalid under most operating conditions.

Whereas it is customary to refer to a gas below its critical temperature as a vapor, in the context of the present specirication a vapor is defined as being in equilibrium with its liquid at a predetermined pressure and temperature. For purposes of this invention the pressure is presumed to be ambient atmospheric pressure. The preferred embodiment of the present invention is intended for use with water vapor, but the general teachings of the invention are equally adaptable for use with other vapors. For example, there are many materials which would find utility in conjunction with the present invention, such as ethyl acetate, Limonene, 2-Butanone (MEK), vanillin, xylene, etc.

Relative humidity is one of the most difficult physical parameters to measure in the real world, particularly high percentage relative humidities, because it is greatly affected by pressure and temperature. Under test conditions, it is even more difficult to control, for an RH measurement taken at one position in a test instrument may be significantly different than the RH in a test chamber even several inches away from the measurement position. When gas conduits and tubes are used to convey humid gases, a temperature change of one or two degrees may be sufficient to saturate the gas to 100% RH, and the accompanying buildup of water in the measuring instrument may completely destroy the test conditions being observed. As an example of this interdependency, the American Society for Testing and Materials (ASTM) standard E-104-85 states that measurement of relative humidity to an accuracy of plus or minus 0.5 percent RH requires a temperature stability of plus or minus 0.1° C. in a closed measurement chamber. Very few laboratories are temperature controlled to this extent, and therefore measurements of the type contemplated herein are required to be made in a system wherein such temperature controls may be achieved.

To a lesser extent, variations in atmospheric pressure affect relative humidity, and it has been found that a good testing procedure requires a control over ambient pressure to within about plus or minus 1 percent of atmospheric pressure. Therefore, a system for testing oxygen permeability should create a pressure drop of no greater than this value.

SUMMARY OF THE INVENTION

The present invention comprises a system for measuring the permeability of a test gas through a membrane under controlled relative humidity conditions, wherein RH is controlled on both sides of the membrane. This system includes an apparatus for generating a carrier gas flow having a known, precisely controlled relative humidity, and for generating a test gas flow having a known, precisely controlled relative humidity, and transmission conduits for transporting the humidity-controlled gases to a test cell; a test cell having two chambers separated by a membrane undergoing test, wherein the carrier gas and the test gas are each admitted into a chamber, and a test gas sensor is located downstream of the test gas chamber, and suitable exhaust conduits enable purging of the test gas from the test cell. The system includes gas flow rate controls and temperature regulation compnents at all points associated with gas transmission paths, to maintain gas temperature at all points in the system higher than the gas temperature in the test cell.

It is therefore a principal object of the present invention to provide a controlled humidity generator for use in conjunction with a gas permeability test cell, to enable the measurement of gas permeability at known humidity conditions.

It is a further object of the present invention to provide a system for measuring gas permeability under controlled humidity conditions, wherein precise control of temperature in all gas flow paths is maintained.

It is another object of the present invention to provide a controlled humidity gas generation apparatus wherein conditions of pressure and temperature are precisely controlled.

The foregoing and other objects and advantages of the invention will become apparent from the following specification and claims, and with reference to the drawings.

BRIEF DESCRIPTION OF THE DRAWING

FIG. 2A shows a block diagram illustrating the flow path through the apparatus;

FIG. 2B shows a temperature profile through the block diagram of FIG. 2A;

FIG. 2C shows a pressure profile through the block diagram of FIG. 2A;

FIG. 7A shows an elevation view of the humidifier portion of the invention;

FIG. 7B shows a rear view of the humidifier of FIG. 7A;

DESCRIPTION OF THE PREFERRED EMBODIMENT

Figure 1:
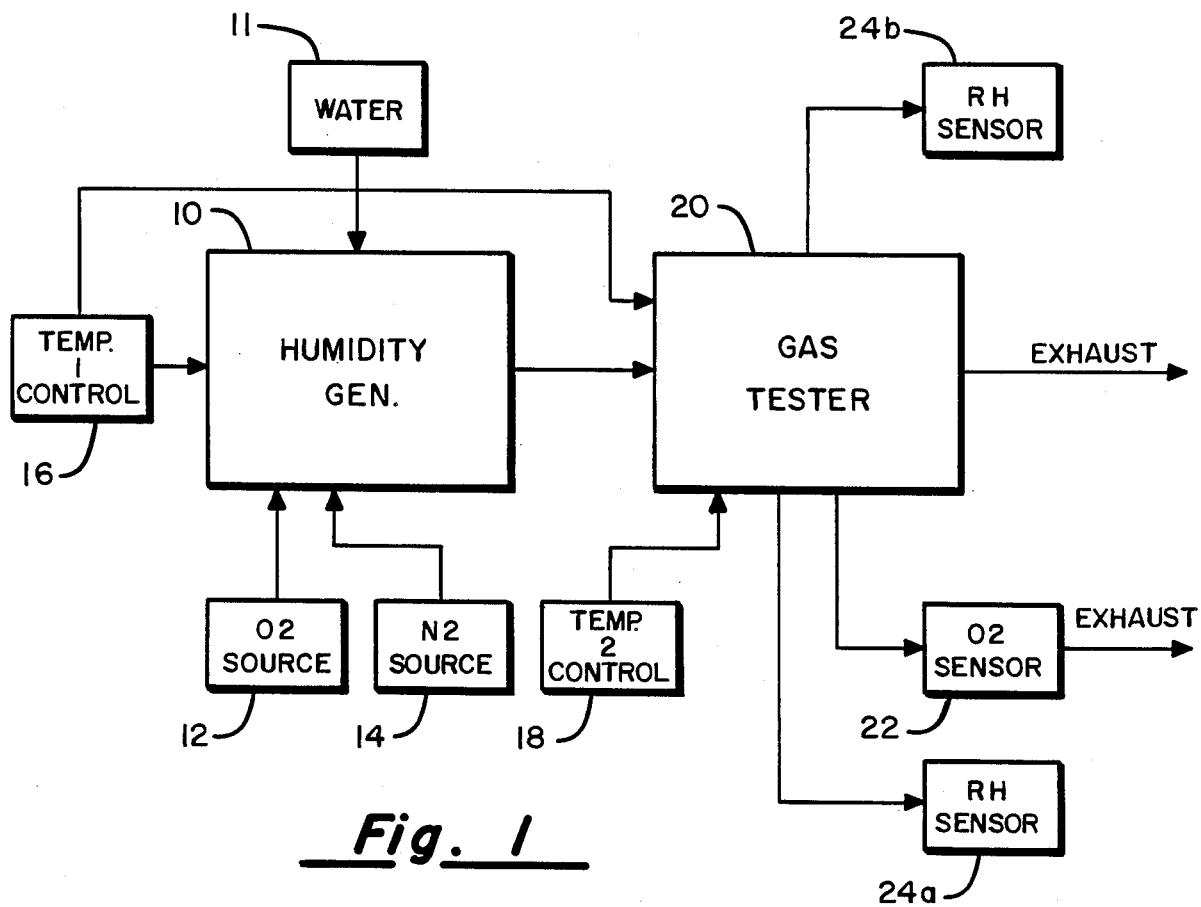
FIG. 1 shows a functional block diagram of the present invention.

Referring first to FIG. 1, there is shown an overall functional block diagram of the invention. The major subsystems of the invention include a humidity generator 10 which functions to develop a source of humidified gas, wherein the humidity may be precisely controlled. The second major subsystem of the invention includes a gas tester 20, which serves to house the particular materials under test so that appropriate permeability measurements may be made through the test materials under the controlled humidity conditions. Oxygen permeability rate may be measured by an $O_2$ sensor 22, and humidity measurements within the test cell 20 may be made by RH sensors 24a and 24b. Both of these RH sensors are sealably incorporated into a test cell to create a virtually leak-free test cell in gas tester 20, or in the case wherein multiple test cells are utilized, the RH sensors may be incorporated into one or more of the multiple test cells. The $O_2$ sensor is typically placed downstream of the test cell in the flow path of the test gas.

The humidity generator 10 requires a first source of dry test gas, preferably oxygen, designated $O_2$ Source 12, and a second source of dry carrier gas, preferably nitrogen with a small amount of hydrogen (2% $H_2$),2% designated $N_2$ Source 14. In addition thereto, humidity generator 10 requires a water input for use in connection with a temperature-controlled water bath to be more fully explained hereinafter. Various temperature control circuits are required in order that precise control over temperature and humidity may be maintained through any given test sequence. For example, a Temp 1 control 16 circuit is utilized to control the actual temperature of the various housing materials associated with the humidity generator 10 and test cell 20. A second temperature control circuit, designated Temp 2 control 18, is used to control the temperature of the gas delivery and transfer conduits throughout the system.

Referring next to FIG. 2A, there is shown a gas flow diagram illustrating the various components through which gas flow must occur in the system. The source gas flows into the system through gas conduits and through humidity bubblers generally formed as a part of the humidity generator 10. Gas flow from the bubblers passes through gas transmission conduits into the gas tester 20. Gas tester 20 has internal gas conduits which pass the gases through each of the several test cells and from there the test gas is passed to an 0₂ sensor, and to an exhaust. Generally speaking, both the test gas and the carrier gas are humidified during passage through the bubblers, and the percentage humidity is measured by means of RH sensors located in one or more of the test cells. The humidified test gas and carrier gas are preferably parallel-coupled to the internal gas conduits of gas tester 20. The amount of gas which is permitted to flow through the RH bubblers is controlled, and is mixed with dry gas from the gas source, the percentage mixture being determined by the measured RH which occurs downstream in the various test cells, since it is the relative humidity in the test cells which is of crucial importance.

Because the various flow paths through the system are subjected to different temperature influences and because it is known that relative humidity is greatly affected by temperature differentials, it is of crucial importance to the system to be able to control the temperature of the gas in the respective conduits and flow passages throughout the system. Temperature is controlled through various temperature control circuits which will be described hereinafter, and reference to FIG. 2B shows the temperature profile throughout the system which is desired. The dotted line profile shown on FIG. 2B represents the idealized temperature profile which would be preferred for the system; the solid line temperature profile shown on FIG. 2B represents actual controlled temperatures throughout the system. In order to avoid condensation caused by saturation, particularly at high operating relative humidities, it is critically important to the system that the temperature in the test cells themselves be maintained at the lowest temperature throughout the system. Therefore, heaters anc other temperature-control mechanisms are utilized to assure that temperatures through the various flow paths illustrated in FIG. 2A are maintained at temperatures elevated from the temperature found in the test cells; this temperature profile relationship is shown on FIG. 2B.

Since it is also known that pressure variations have an effect on relative humidity, it is important that pressure drops be controlled throughout the svstem. FIG. 2C shows an idealized pressure profile in dotted line format, and an actual pressure profile is shown in solid line. It is preferable that the pressure through the entire gas tester 20 be maintained at a substantially constant value, but in practical applications it has been found that a pressure drop ($\Delta P$) on the order of 1 percent of ambient pressure is suitable for purposes of this invention. The pressure profile of FIG. 2C illustrates this effect, wherein $\Delta P$ is less than or equal to 0.15 psi.

Figure 3:
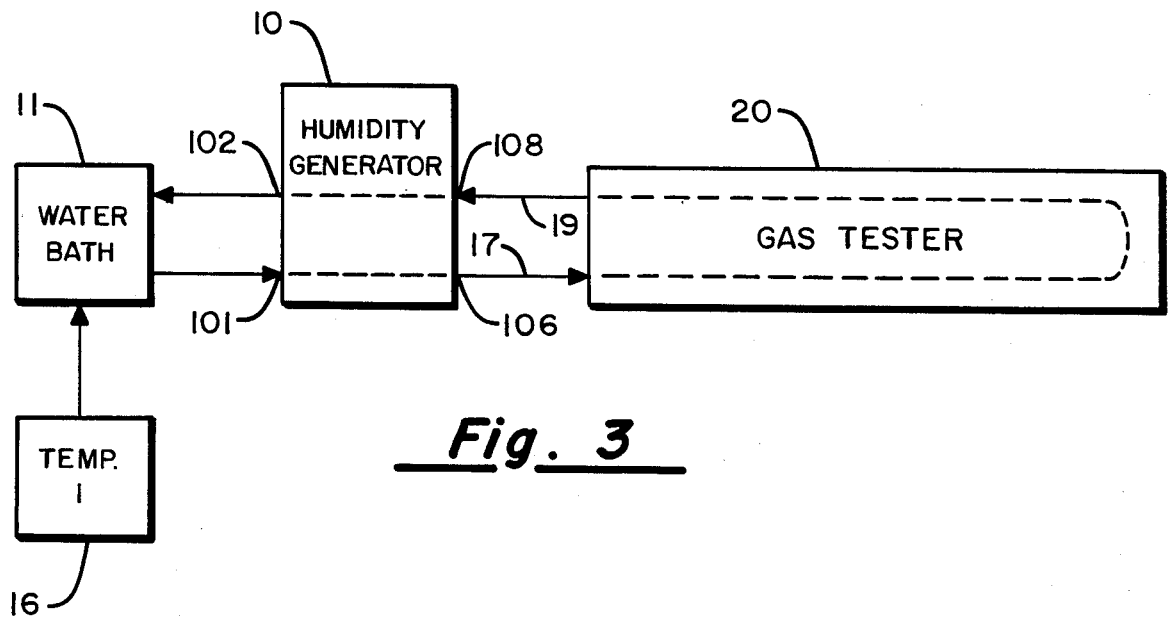
FIG. 3 shows a simplified diagram of one form of temperature control.

FIG. 3 shows one form of temperature control in simplified diagrammatic illustration. A water bath 11 is coupled to a water line which passes through numidity generator 10, and then passes through conduit 17 to gas tester 20, forming a balanced loop through the gas tester, returned to humidity generator 10 and finally through conduit 19, returning to the water bath. The purpose of the balanced loop temperature control illustrated in FIG. 3 is to attempt to maintain the temperature of the humidity generator 10 as nearly as possible identical to the temperature of gas tester 20. By keeping these temperatures as close as possible it becomes simpler to control the vital parameters; namely, that of requiring the temperature within the respective test cells in gas tester 20 to be the lowest temperatures in the system. It has been found that the more elevated the humidity generator 10 is in temperature as compared with the test cell temperature, the more difficult it becomes to adjust the vapor mixture to producevery low vapor pressures, particularly at higher temperatures. Also, there is a greater risk of accidental condensation in the test cell if the temperatures in the humidity generator 10 are elevated, especially if the dry gas flow into the test cell is impeded or momentarily changes. The balanced loop system enables the humidity generator 10 to be physically separated from the gas tester 20 so as to maintain the temperature in the humidity generator 10 slightly above the temperature in the test cells. Water maintained at a constant temperature in the water bath 11 by TEMP 1 control circuit 16 is passed through the water lines illustrated in FIG. 3, and the water lines are physically positioned relative to the gas flow transmission paths so as to have a symmetrical and balanced influence on temperature in the gas flow transmission paths. The thermal loss and/or gain is identical along both the incoming and outgoing legs of the water line, and therefore the temperature in the humidity generator housing and in the test cell housing reaches a balanced average condition.

The present invention utilizes a vapor generator produced by the "two flow method" to generate a wide range of vapor pressures. In this technique there are two streams of gas, one stream being a dry gas and the other being a stream of water-saturated gas. When the two streams are combined the relative humidity is produced by the ratio of the flow division, although it is not necessary to maintain an accurate metering of the relative flows in order to generate accurate relative humidity levels. Instead, the design of the invention is intended to produce consistently stable vapor pressure levels over a wide range of temperatures. The relative humidity is measured in the test cell itself, and the metering flow rate of the two gas streams may be adjusted by virtue of this measurement.

Matched volume flow control devices will maintain a stable mixing ratio if they are kept at the same temperature and pressure. In the present invention this is easily accomplished because the volume flow meters are placed in the dry gas lines before the humidity generator 10, and therefore both flow meters are exposed to ambient temperature. When the ambient temperature varies the volume flow through these flow control devices change in the same direction, therefore maintaining the same mixing ratio of the wet and dry gases. A slight change in the total volume and mass flow through the system may be caused by ambient temperature changes, but this is not sufficient to adversely effect the test conditions. Alternatively, mass flow controllers could be used with the present invention instead of volume flow controllers.

Figure 4:
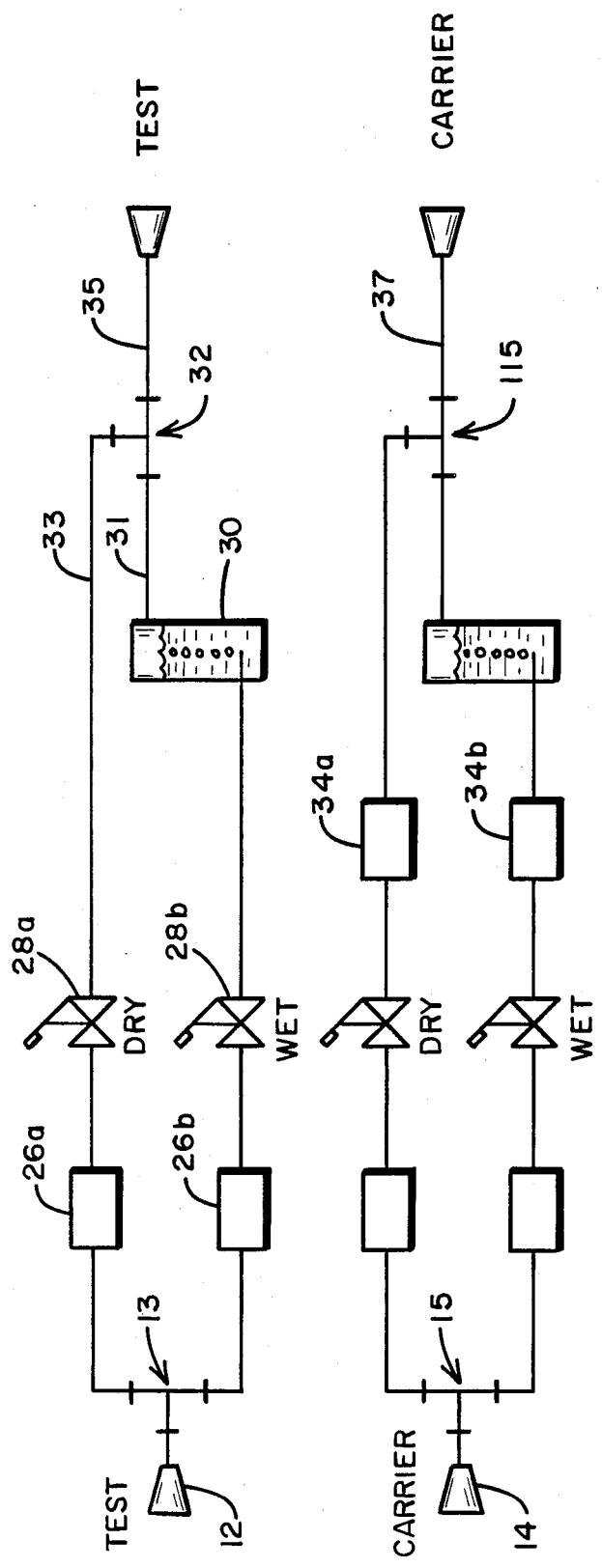
FIG. 4 shows a further flow diagram illustrating the gas flow circuit of the present invention.

FIG. 4 shows a flow diagram of the test gas and the carrier gas through the humidity generator 10. For purposes of description herein it will be presumed that the test gas is oxygen, which is derived from an $O_2$ Source 12. The carrier gas is presumed to be nitrogen, which is derived from an $N_2$ source 14. Each of these source gases is fed into humidity generator 10, and is divided into two parallel flow paths. Each of the parallel flow path legs has a flow controller inserted therein, in order that the flow rate through the respective legs may be precisely controlled. A flow valve may be incorporated into each line in order to provide manual control over flow rates.

Since the parallel flow paths for the carrier gas and the test gas are virtually identical, except as set forth below, the description herein will be made only with reference to the test gas parallel flow path legs. The test gas is passed from $O_2$ source 12 into two parallel conduits by a "T" connection 13, each of which being coupled to a flow controller 26a, 26b. Flow controllers 26a, 26b, are commercially available components, as for example, Model FC280, manufactured by Tylan Inc., Carson, Calif., or Model SF031MOZZ-14G, manufactured by Aalborg Instruments, Monsey, New York. Each of these flow controllers precisely control the flow rate of the gases passing through them, by means of a controllable valve 28a, 28b. The gas flow from valve 28b is coupled into a water bubbler 30, which is a sealed container substantially filled with water. The inlet to bubbler 30 from valve 28b is proximate the lowest water level, thereby permitting the gas to bubble upwardly toward the water surface. The outlet from bubbler 30 is coupled to a gas conduit 31. The gas outlet from valve 28a is coupled to a gas conduit 33, which is joined to gas conduit 31 at T-connection 32. The dry gas via conduit 33 and the humidified gas via conduit 31 are mixed at T-connection 32, and passed therefrom via conduit 35.

The parallel carrier gas flow lines each have a catalyst trap 34a, 34b therein, in order to filter out any stray $O_2$ which might be accumulated in either the $N_2$ source or the flow lines. Except for this distinction, the flow paths for the oxygen test gas lines are identical to the flow paths for the nitrogen carrier gas lines. In each case, one of the parallel flow lines is coupled into a bubbler, wherein the gas is bubbled through a volume of water and is humidified thereby. The humidified gas passes from the bubbler to rejoin the parallel dry gas line, and to become mixed therewith. The mixed and humidified gas is then conveyed into gas tester 20 as will be hereinafter described. The relative amounts of dry gas and wet gas can be closely controlled by adjusting the respective valves in the gas flow lines; see, for example, valves 28a, 28b with respect to the test gas flow lines. The catalyst traps 34a, 34b are commercially available components, as for example Model 1253701, manufactured by Englehard Industries, Skokie, Illinois. The output from humidity generator 10 is a flow rate of mixed, humidified test gas which flows through conduit 35, and a similar output of mixed, humidified carrier gas which flows through conduit 37. As hereinbefore described, the relative humidity of each of these gases may be closely controlled by measuring humidity in the downstream test cells and adjusting the respective valves.

Figure 5A:
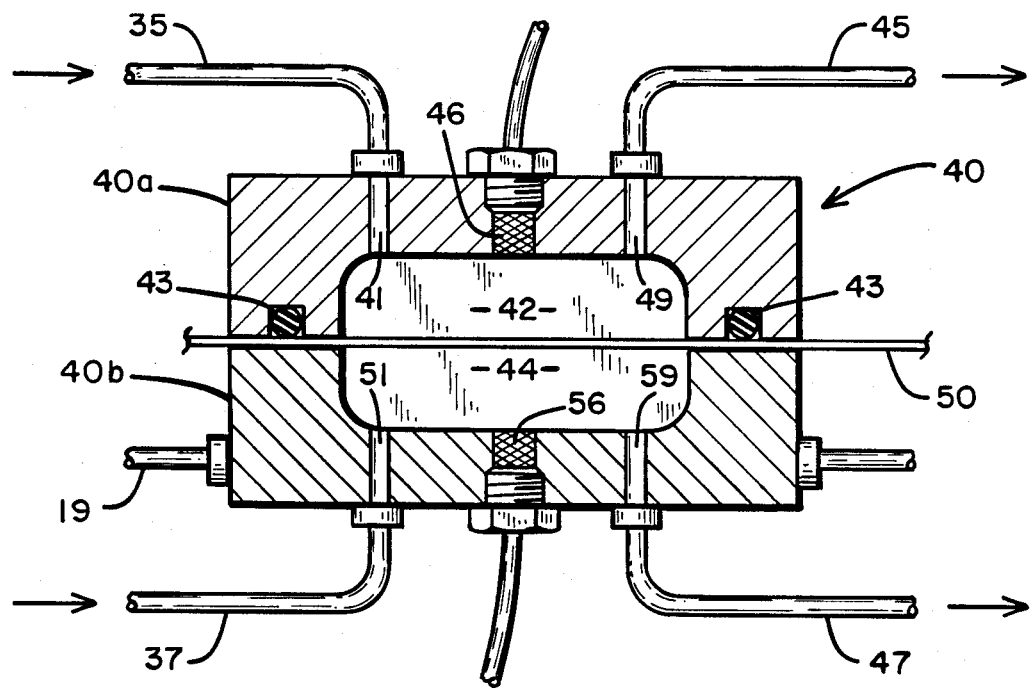
FIG. 5A shwws a cross-section view of a typical test cell for use with the invention.

Referring next to FIG. 5A, there is shown a cross section view of a single test cell 40, which may form a part of gas tester 20. Test cell 40 is formed of two separable housings, housing 40a and housing 40b, which may be sealably clamped together (not shown), and which has preferably at least one O-ring 43 to assure a gas tight connection between the respective housings. In operational use, a plastic membrane 50 is clamped between housings 40a and 40b, membrane 50 being a sample of the plastic material which is to undergo the permeability test hereinafter described. As a result of the barrier formed by membrane 50 there is formed in the interior of test cell 40 an upper chamber 42 and a lower chamber 44.

Upper chamber 42 has an inlet passage 41 coupled to conduit 35, thereby permitting the flow of test gas into chamber 42. An outlet passage 49 passes from chamber 42, and is coupled to outlet conduit 45, to thereby permit the exit flow of test gas from test cell 40. An RH sensor 46 is sealably attached and exposed to the interior of chamber 42, sensor 46 having connection to appropriate circuits (not shown) for purposes of accurately measuring the relative humidity within chamber 42.

Lower chamber 44 has passages similar to upper chamber 42, as for example inlet passage 51 which is coupled to conduit 37 to thereby permit the inflow of a carrier gas into chamber 44. An outlet passage 59 is coupled to conduit 47 to permit the outflow of a carrier gas from chamber 44. An RH sensor 56 is sealably coupled to the interior of chamber 44 for the purpose of accurately measuring the relative humidity in chamber 44.

Conduit 47 is coupled to an oxygen sensor of a type which is known in the art. For example, an oxygen sensor of the type described in U.S. Pat. No. 3,223,597, issued Dec. 14, 1965. Conduit 45 may be passed directly to an exhaust. In operation, the flow of the test gas into test cell 40 via conduit 35 results in upper chamber 42 becoming filled with the test gas, and the entire upper surface area of membrane 50 is thereby exposed to the test gas. The flow of the carrier gas via conduit 37 similarly fills the lower chamber 44 of test cell 40. The permeability of the membrane 50 permits a certain quantity of the test gas in upper chamber 42 to permeate downwardly into lower chamber 44, and to flow out through conduit 47 to the $O_2$ sensor connected thereto. The $O_2$ sensor, through principles which are well known in the art, is able to detect very minute quantities of the oxygen which has permeated through membrane 50, and a measure of this permeability is thereby obtained. The humidity in upper chamber 42 is closely monitored by RH sensor 46, and the humidity in lower chamber 44 is similarly closely monitored by RH sensor 56. Both RH sensor 46 and RH sensor 56 may be coupled to appropriate circuitry which ultimately controls the flow valves associated with the flow controllers in humidity generator 10 (see FIG. 4), or alternatively the flow controllers may be adjusted manually. The respective flow controllers or valves are adjusted to assure the desired relative humidity in upper and lower chambers 42 and 44, and also to achieve a predetermined relative humidity, as determined by the test set-up conditions for the particular test in question. In this manner, the permeability of membrane 50 can be tested under precisely controlled conditions of relative humidity on both sides of membrane 50.

Figure 5B:
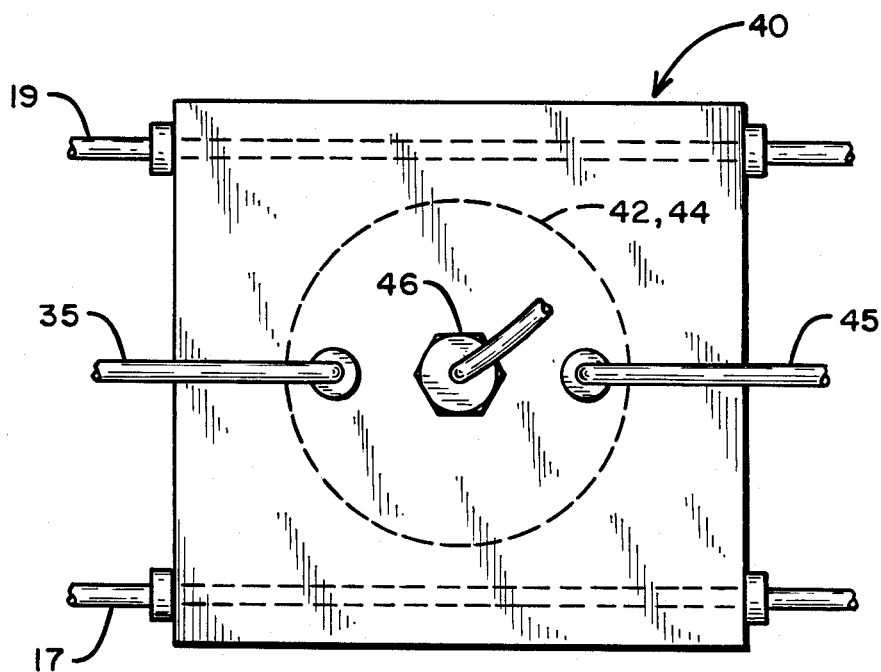
FIG. 5B shows a top view of a typical test cell.

FIG. 5B shows a top view of a representative test cell 40, illustrating the respective gas and temperature control connections. Conduit 17 carries water from the temperature-controlled water bath 11 into the housing or housings forming test cell 40, and thereafter into an adjoining test cell. Conduit 19 comprises the return path for water to water bath 11, being coupled to similar conduits in adjacent test cells. Conduits 17 and 19 are placed in very close physical relation to the respective housings forming test cell 40, and other test cells, in order that good temperature conductivity may be maintained between the water passing through the conduits and the housing materials.

Figure 6:
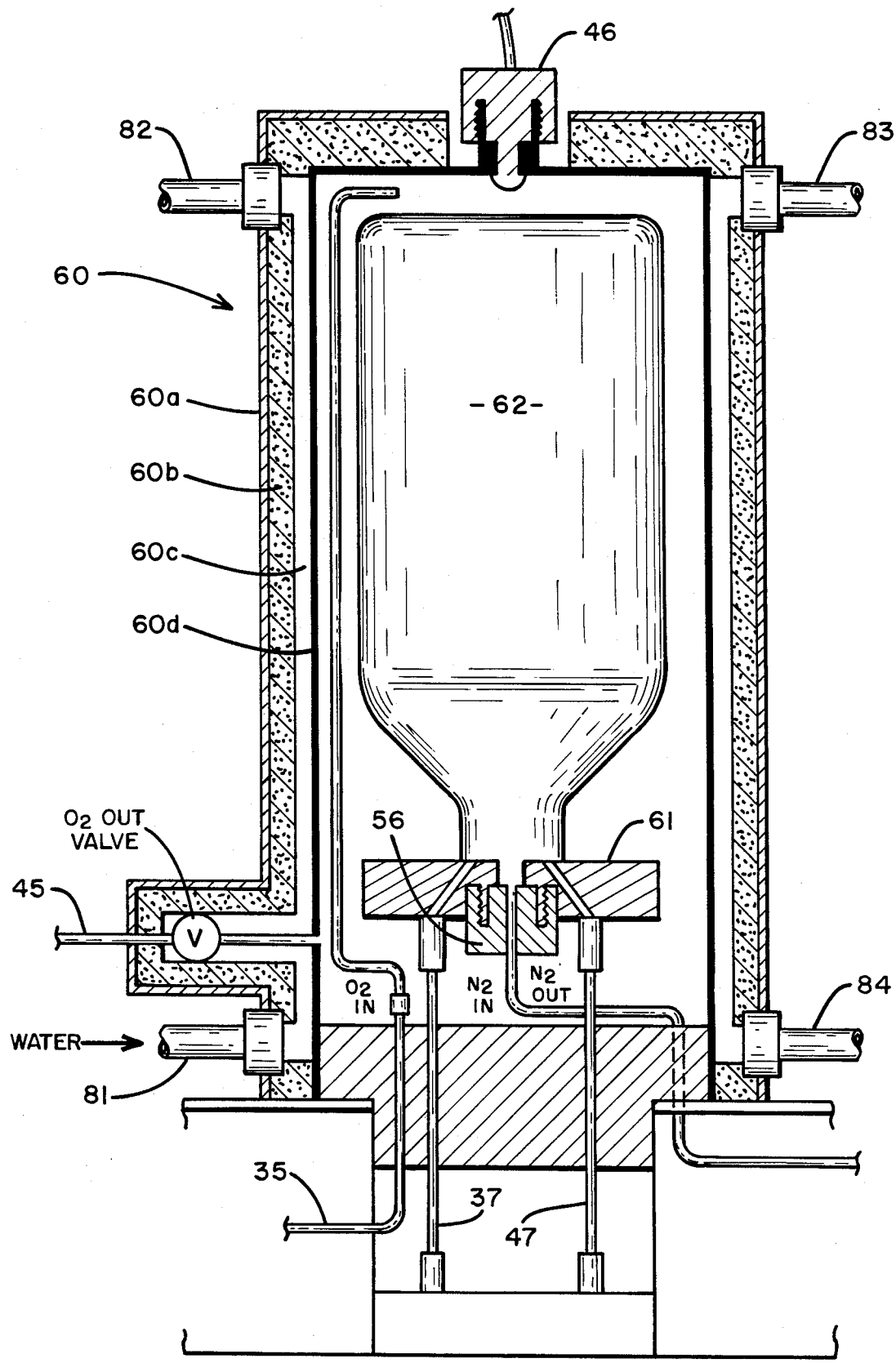
FIG. 6 shows a diagram of a further typical test cell.

Referring next to FIG. 6, there is shown a further form of gas tester which may be utilized for permeability testing of containers of various types. An outer chamber 60 is sized to enclose various test components to be hereinafter described. The container under test is designated as 62 which may be, for example, a plastic bottle of specified configuration. Container 62 is sealably affixed by a seal 61 within chamber 60, and carrier gas conduit 37 passes through the floor to the interior of container 62. An exit carrier gas conduit 47 also passes into the interior of container 62, to remove carrier gas therefrom. A test gas conduit 35 passes through the wall of outer chamber 60 to the interior of the chamber, and an exit conduit 45 exhausts the test gas therefrom via a suitable valve. An RH sensor 46 is positioned inside of outer chamber 60, to maintain a careful measure of the RH of the test gas within chamber 60. Similarly, an RH sensor 56 is affixed to and exposed to the interior of container 62 to carefully monitor the relative humidity within container 62. In operation, which is similar to that described hereinbefore, the humidified test gas is passed to the interior of outer chamber 60 via conduit 35, and is exhausted therefrom via conduit 45. The interior volume of outer chamber 60 eventually becomes uniformly filled with the humidified test gas, which in the preferred embodiment is presumed to be oxygen. The carrier gas is passed to the interior of the container 62 via conduit 37, and is exhausted therefrom via conduit 47. Conduit 47 is coupled to an oxygen sensor of the type described hereinbefore. The relative humidity of the carrier gas inside of container 62 is carefully measured, and the relative humidities of both the carrier gas and the test gas are controlled as has been hereinbefore described. To the extent that oxygen permeates container 62, trace quantities of oxygen will be picked up by the carrier gas and passed to the $O_2$ sensor via conduit 47, and a measurement of permeability will thereby be obtained, under the conditions of the closely controlled humidity which has been selected for the test.

Outer chamber 60 is constructed of a number of layers in order to maintain good control over temperature. For example, an outer skin 60a is preferably constructed of metal such as aluminum or stainless steel. An interior layer 60b is formed of insulation in order to provide good temperature insulation about the test chamber. A water channel 60c is created between insulation layer 60b and an interior chamber 60d. Interior chamber 60d is preferably constructed of copper or other metal capable of good heat conductivity. A plurality of water inlets and outlets 81, 82, 83, and 84 are provided for coupling to a suitable water bath, in order that water may be passed through water channel 60c to maintain inner layer 60d at a controlled temperature. If a plurality of such chambers 60 are incorporated into a single system, the respective water inlets and outlets 81–84 may be connected in a series loop configuration, along the lines illustrated in conjunction with FIG. 3.

Figure 8:
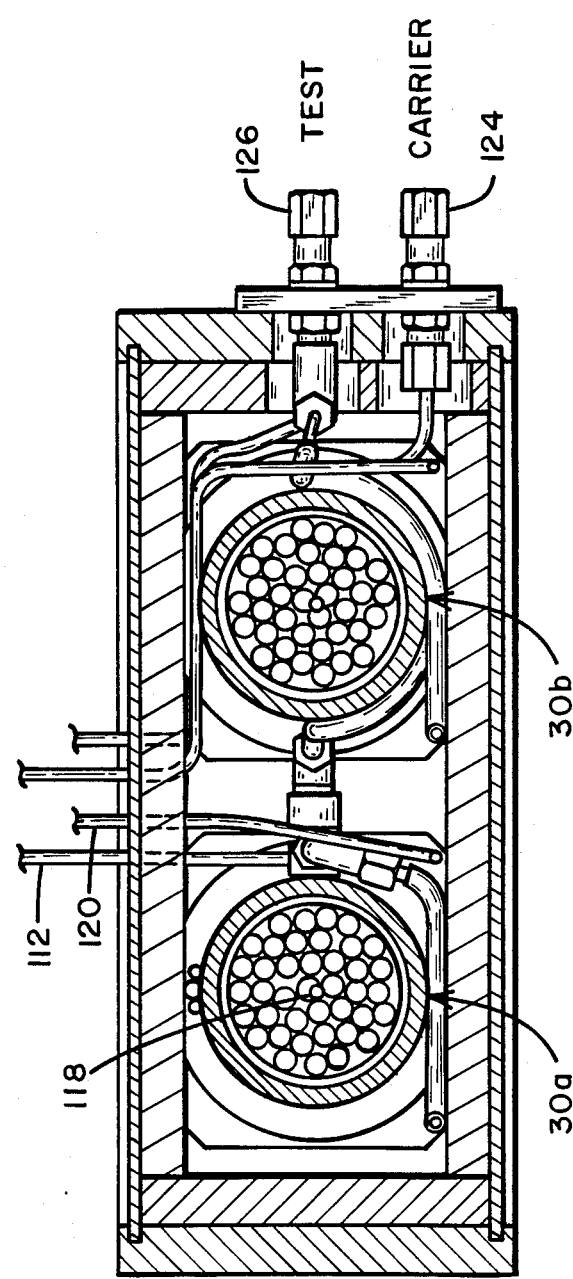
FIG. 8 shows a cross section view taken along the lines 8—8 of FIG. 7A.

FIGS. 7A, 7B and 8 show construction details of the humidity generator 10. FIG. 7A shows a side elevational view of humidity generator 10, FIG. 7B shows a rear elevational view of humidity generator 10, and FIG. 8 shows a cross-section view taken along the lines 8—8 of FIG. 7A. Humidity generator 10 includes a carrier gas water bubbler 30a and a test gas water bubbler 30b, and the associated conduits necessary to convey the test and carrier gases through humidity generator 10. Humidity generator 10 also includes water conduits which circulate water from water bath 11 through humidity generator 10 in close proximity to the water bubblers in order to maintain the temperature control. A water inlet 101 is coupled to the water bath 11 for receiving temperature-controlled water; a water outlet 102 recirculates the water back to the water bath.

Water inlet 101 is coupled to a conduit 103, preferably made from copper tubing or like material which has good temperature conductivity. Conduit 103 is placed in close physical contact with carrier gas water bubbler 30a in order to maintain good temperature conductivity therebetween. The outer casing of water bubbler 30a is preferably made from a copper tube, and conduit 103 is preferably affixed to the copper tube by soldering and means of straps 104 or similar attachment devices. Conduit 103 passes upwardly in close physical proximity to the outer casing of water bubbler 30a, bridges across the top of water bubbler 30a and across the top of water bubbler 30b, and then is downwardly positioned in close physical proximity to water bubbler 30b until it connects to a gas tester outlet 106. Further conduits convey the water through a circulatory path gas tester 20, retrning the water to inlet 108. Inlet 108 and water outlet 102 are interconnected through a conduit (not shown) on the reverse side of water bubblers 30a and 30b, which conduit follows the same paths as the path described above for conduit 103. Water outlet 102 is connected to a return conduit to the water bath 11.

The test gas and the carrier gas are also connected to humidity generator 10, each gas flowing through a respective water bubbler and associated conduits, before being conveyed to the gas tester 20. The paths of travel for the carrier gas and the test gas are virtually identical, and will be described in detail with respect to the carrier gas. It is understood that the test gas follows a similar path with respect to gas flow within humidity generator 10.

To understand the flow of carrier gas and test gas within the humidity generator 10, reference should also be made to FIG. 4, which illustrates the gas flow paths in schematic diagram. FIG. 4 illustrates that, for each type of gas, there exists a "dry" flow path and a "wet" flow path; both of these flow paths may be found within humidity generator 10, as hereinafter described. The flow paths of the carrier gas will be described with reference to FIG. 4 and to FIGS. 7A, 7B and 8, which carrier gas is associated with carrier gas water bubbler 30a.

The carrier gas is initially confined in a gas source, as for example nitrogen source 14 (see FIG. 1). A conduit connected to source 14 is diverted into two identical branches through a "T" connection 15 (see FIG. 4). Both conduits extending from this "T" connection 15 pass through flow controllers, as have been hereinbefore described, and thereafter pass into humidity generator 10 through inlet connections adapted for that purpose. The "dry" carrier gas passes into conduit 110, and from there into a "T" connection 115, where it is mixed with the "wet" carrier gas to be hereinafter described. The "wet" carrier gas passes into conduit 112 in humidity generator 10, and thereafter upwardly to a connection into manifold 114. Manifold 114 has an outlet 116 which is sealed inside of gas bubbler 30a. A conduit 118 is sealably connected to outlet 116, and conduit 118 passes downwardly to the bottom of gas bubbler 30a. Conduit 118 is open at its bottom end, thereby permitting gas to flow outwardly therefrom into the water filling the inside of bubbler 30a. The gas from conduit 118 therefore bubbles upwardly to the surface of the water therein, producing a highly humidified atmosphere in the region above the water surface. A second opening through manifold 114 is exposed to this humidified gas region, and some of the humidified gas is conveyed therethrough to a conduit 120 attached to manifold 114. Conduit 120 is coupled at its other end to "T" connector 115, thereby permitting the humidified gas in conduit 120 to become mixed with the dry gas in conduit 110. "T" connector 115 has an outlet conduit 122 which conveys the mixed gas to a carrier gas outlet 124. Carrier gas outlet 124 is connected through suitable conduits to gas tester 120, as has hereinbefore been described.

The flow paths associated with the test gas are virtually identical to those described with respect to the carrier gas, with the exception that the test gas, of course, flows through gas bubbler 30b and ultimately is delivered at test gas outlet 126.

The gas flow paths described hereinabove are maintained at very carefully controlled temperatures, as closely as possible to the temperature maintained by the water bath. This is especially true of the mixed gas which contains proportionate quantities of dry gas and humidified gas. In order to better maintain temperature control over this mixed gas, the conduit 122, for example, is made from stainless steel which is encased within a copper tube. The copper tube is itself directly affixed to the copper casing about a bubbler (30a or 30b) to provide good heat conductivity between the copper tube and the copper casing, so that the temperature of the gas within conduit 122 may be maintained as closely as possible to the same temperature as bubbler 30a or 30b.

Figure 9:
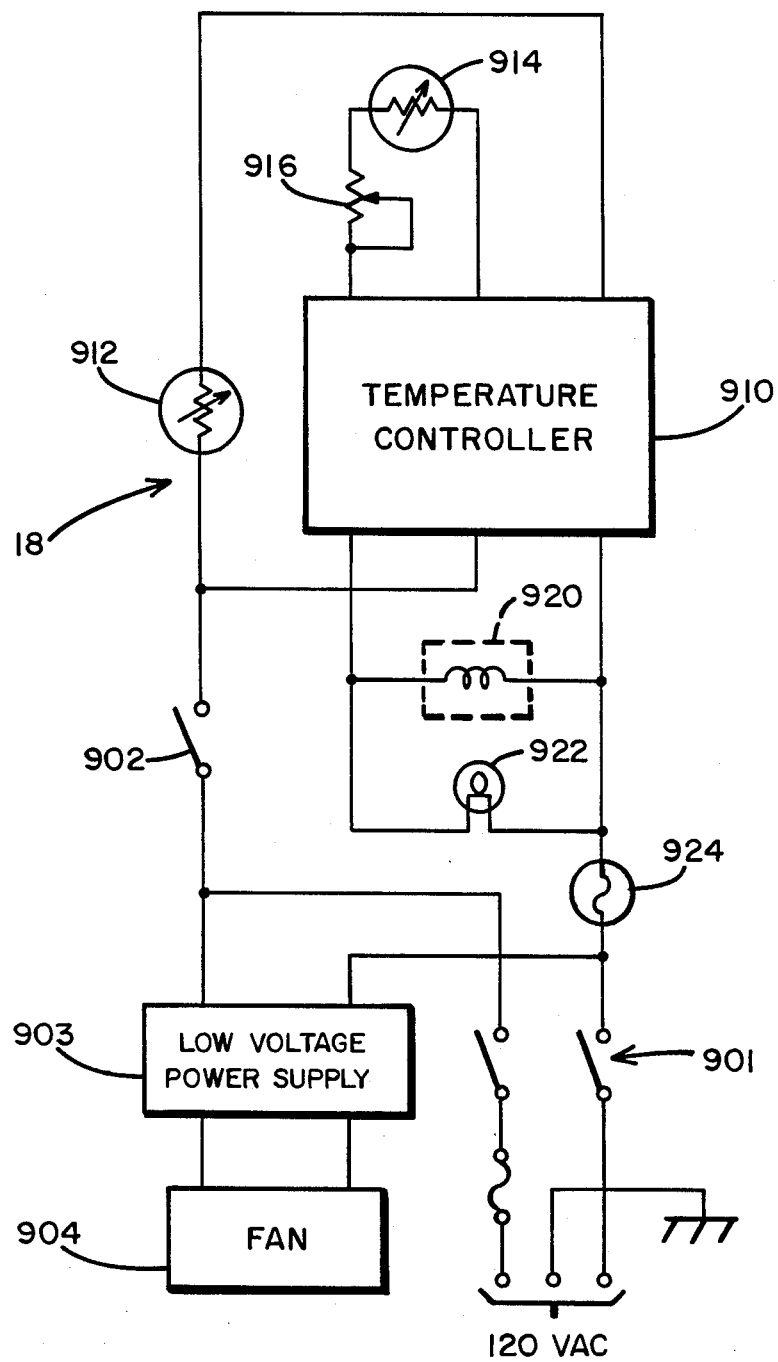
FIG. 9 shnows an electrical schematic of certain heating circuits of the present invention.

FIG. 9 shows an electrical schematic of one form of heating circuit suitable for use with the present invention, in particular a schematic suitable for use as a Temp 2 control 18 (see FIG. 1). The circuit operates from 120V, alternating current, commercially supplied power and is activated by power switch 901. Power switch 901 applies power to energize a low-voltage power supply 903, which is used to power a low-voltage fan 904. Fan 904 is preferably placed in proximity to the gas conduit and heater 920 found in gas tester 20, in order that air temperature circulating about these gas conduits may be kept uniformly constant.

Switch 902 is a heater switch for activating temperature controller 910 and its associated heaters and indicators. Temperature controller 910 may be a commercially available temperature control circuit, as for example Model TCR 4B, manufactured by SSAC Inc., Liverpool, New York. Temperature controller 910 utilizes one or more thermistors 912, each preferably placed in proximity with a test cell found within gas tester 20. A further thermistor 914 may be placed in proximity to the air circulation path affected by fan 904, so as to provide an offset temperature set point control for the air flow in and around the gas conduits of gas tester 20. Each thermistor 914 may be selectively adjusted to provide an offset temperature control set point by means of variable resistance 916. That temperature offset is higher than the temperature indication provided by thermistor 912. An electrical heater 920 as preferably placed in temperature contact with the gas conduits which lead into the respective test cells, and heater 920 is controllable by a high limit thermostat 924. Heater 920 and thermostat 924 may be commercially available components, as for example a heater manufactured by Minnco Products, Minneapolis, Minnesota, under Part No. HR 5168; and a thermostat manufactured by Portage Electric Products, under Part No. A-21E+060F. A neon indicator 922 is provided as an indicator that power is being applied to heater 920 via temperature controller 910.

The temperature control circuits of FIG. 9 are used to regulate the temperature of the respective gas conduits and flow paths leading to test cells within gas tester 20, in order to insure that the temperature at all flow points in the system is kept elevated above the temperature within the respective test cells.

In operation, it is necessary first to establish relatively constant end control temperature conditions throughout the system. This is accomplished by adjusting the temperature-controlled water bath and initiating a flow of water to cycle through the various water conduits in the system. Next, the electrical heater controls are automatically adjusted to provide the necessary temperature differential between the test cells and the other system components, particularly the conduits and transmission lines for passing the test gas and the carrier gas. Once the temperature has stabilized, and the test cells are maintained at a temperature cooler than exists elsewhere in the gas transmission paths of the system, the operational test process can begin. It is presumed that a suitable membrane to undergo a test has been placed into the test cell or cells, and the operational test proceeds with the admittance of a test and carrier gas into the system. The water bubblers are activated and the respective flow controllers are adjusted to provide the required degree of relative humidity to the gases, relative humidity being determined by inspection of suitable indicators connected to the RH sensors in the test cells. The flow valves associated with the flow controllers may be adjusted in order to adjust relative humidity, and it is usually preferably to adjust the relative humidity of the test gas to be substantially the same as the relative humidity of the carrier gas. After the system has stabilized in this regard, the carrier gas may be coupled into a conduit leading to the sensor which has been installed to read the quantity of test gas which has permeated through the membrane into the carrier gas. In most situations, the test gas will be oxygen and the carrier gas will be nitrogen, and in this situation an oxygen sensor is provided and coupled to the nitrogen conduit outlets from the test cells to provide a measurement of the amount of oxygen which has permeated into the nitrogen gas. Adjustment of the flow controllers and valves associated with controlling the flow of gas into the water bubblers permits tests to be conducted at various relative humidities, although usually the relative humidities of interest are quite close to saturation of 100 percent.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A system for controllably measuring permeability of a test gas through a membrane under conditions of controllable relative humidity of the test gas, wherein the test gas is obtained from a source of dry test gas, comprising:
   (a) a gas bubbler means for bubbling said dry gas through a liquid-filled container to form a humidified test gas reservoir;
   (b) a gas conduit coupled between said source of dry gas and said gas bubbler, said gas conduit including means for diverting a portion of said dry gas from entering said gas bubbler means;
   (c) means for controllably connecting and mixing dry test gas from said means for diverting and from said humidified test gas reservoir, and for conveying said mixed dry and humidified test gas;
   (d) a test cell having a first chamber connected to said means for conveying said mixed dry and humidified test gas, and having a second chamber, said first and second chambers being separated by a membrane;
   (e) a gas sensor coupled to said second chamber, said gas sensor being adapted to measure trace amounts of said test gas; and
   (f) temperature control means connected to said gas bubbler means, said gas conduit, said means for conveying said mixed dry and humidified test gas and said test cell, said temperature control means having further means for controlling the temperature of said test gas and for insuring that the temperature of said test gas in said test cell is lower than the temperature of said test gas in all other elements connected by said temperature control means.

2. The system of claim 1, further comprising means for measuring the relative humidity of said test gas in said first chamber of said test cell.

3. The system of claim 2, further comprising means for adjusting the flow rate of said test gas from said source of dry test gas.

4. The system of claim 3, wherein said means for adjusting the flow rate further comprises a mass flow controller.

5. The system of claim 4, further comprising means for controlling the pressure drop of said test gas between said source of dry test gas and said test cell.

6. A system for measuring the gas permeability of a membrane under conditions of controlled humidity of said gas, by controllably admitting a flow of humidified test gas into a firstchamber and controllably admitting a flow of carrier gas into a second chamber, the first and second chambers being separated by said membrane, comprising:
   (a) a source of dry test gas and a source of dry carrier gas;
   (b) a first gas bubbler connected to said source of dry test gas, and a second gas bubbler connected to said source of dry carrier gas; each of said first and second gas bubblers having means for bubbling said connected gas through a liquid reservoir and for collecting said gas above said liquid reservoir in a humidified gas reservoir;
   (c) first means for controlling the temperature of the gas in each of said humidified gas reservoirs;
   (d) a first gas mixer coupled between said source of dry test gas and said first gas bubbler humidified gas reservoir, including means for controllably mixing a flow of dry test gas with a flow of humidified test gas; a second gas mixer coupled between said source of dry carrier gas and said second gas bubbler humidified gas reservoir, including means for controllably mixing a flow of dry carrier gas with a flow of humidified carrier gas;
   (e) second means for controlling the temperature of the respective controllably mixed test and carrier gases;
   (f) a first gas conduit coupled between said first gas mixer and said first chambe;; a second gas conduit coupled between said second gas mixer and said second chamber;
   (g) third means for controlling the temperature of the respective gases in the first and second conduits;
   (h) fourth means for controlling the temperature of the respective gases in said first and second chambers;
   (i) means coupled to said second chamber for measuring trace quantities of said test gas in said second chamber; and (j) means for adjusting said first, second, third and fourth means for controlling temperature to insure that the gas temperature in said first and second chambers is the lowest of all controlled temperatures.

7. A system as claimed in claim 6, wherein said first and second gas mixer each further comprise a flow control valve.

8. The system of claim 6, further comprising first means for measuring relative humidity coupled to said first chamber, and second means for measuring relative humidity coupled to said second chamber.

9. The system of claim 8, further comprising means for selectively adjusting each of said first and second gas mixer for controllably mixing in response to said respective first and second means for measuring relative humidity.

10. The system of claim 8, wherein said first means for controlling the temperature of the gas in each of said humidified gas reservoirs further comprises a water bath maintained at a controlled temperature and water conduits coupled to said water bath and affixed to said first and second gas bubblers in heat conduction relationship.

11. The system of claim 10, wherein said second means for controlling the temperature further comprises further water conduits coupled to said water bath and affixed to said gas mixers in heat conduction relationship.

12. The system of claim 11, wherein said third means for controlling the temperature further comprises further water conduits coupled to said water bath and affixed to said first and second gas conduits in heat conduction relationship.

13. The system of claim 12, wherein said fourth means for controlling the temperature further comprises further water conduits coupled to said water bath and affixed adjacent said first and second chambers in heat conduction relationship.

* * * * *